United States Patent [19]

Fujita

[11] Patent Number: 4,982,338

[45] Date of Patent: Jan. 1, 1991

[54] METHOD FOR PROCESSING INFORMATION ON CHEMICAL REACTIONS

[75] Inventor: Shinsaku Fujita, Minami-ashigara, Japan

[73] Assignee: Fuji Photo Film Co., Ltd., Minami-ahsigara, Japan

[21] Appl. No.: 368,919

[22] Filed: Jun. 16, 1989

Related U.S. Application Data

[63] Continuation of Ser. No. 895,864, Aug. 12, 1986, abandoned.

[30] Foreign Application Priority Data

Aug. 12, 1985 [JP] Japan ................................ 60-177345
Aug. 16, 1985 [JP] Japan ................................ 60-180874
Aug. 16, 1985 [JP] Japan ................................ 60-185386

[51] Int. Cl.$^5$ .......................................... G06F 15/20
[52] U.S. Cl. ................................... 364/497; 364/496
[58] Field of Search ............... 364/496, 498, 497, 200, 364/900, 300

[56] References Cited

U.S. PATENT DOCUMENTS

| | | | |
|---|---|---|---|
| 4,085,443 | 4/1978 | Dubois et al. ...................... | 364/900 |
| 4,205,391 | 5/1980 | Ulyanov et al. .................... | 364/496 |
| 4,365,303 | 12/1982 | Hannah et al. .................... | 364/498 |
| 4,473,890 | 9/1984 | Araki ................................. | 364/900 |
| 4,642,762 | 2/1987 | Fisanick ............................ | 364/300 |
| 4,747,059 | 5/1988 | Hirayama et al. ................. | 364/900 |

OTHER PUBLICATIONS

Barnard et al., "Computer Storage and Retrieval of Generic Structures in Chemical Patents. 4. An Extended Connection Table Representation for Generic Structures", 4/5/82, pp. 160–164.

Krishnamurthy, "Wisenom. A Formal Organic Chemical Nomenclature System", 4/28/81, pp. 152–159.

Skulnik, "A Multilingual Index Via the Multiterm System", 2/26/72, pp. 128–133.

"The Description of Organic Reactions Based on Imaginary Transition Structures", *Pure and Applied Chem.*, vol. 62, No. 3, pp. 605–608 (1989).

*Journal of Synthetic Organic Chemistry, Japan*, vol. 47, No. 5, (1989)—English translation of Japanese article written by Applicant.

*Primary Examiner*—Parshotam S. Lall
*Assistant Examiner*—Ellis B. Ramirez
*Attorney, Agent, or Firm*—Sixbey, Friedman, Leedom & Ferguson

[57] ABSTRACT

There is disclosed a method for recording and storing information on chemical reactions of producing at least one product from at least one starting material, which comprises representing the chemical reaction in such a manner that the starting material is topologically superposed upon the product, and bonds are distinguished and classified into three categories of (1) bonds linking two nodes appearing both in the starting and product stages, (2) bonds linking two nodes appearing only in the starting stage and (3) bonds linking two nodes appearing only in the product stage. Methods for processing information on chemical reactions to record and store, which include preparing an imaginary transition structure (ITS) of a chemical reaction and a connection table of ITS according to the representation are also disclosed.

4 Claims, 1 Drawing Sheet

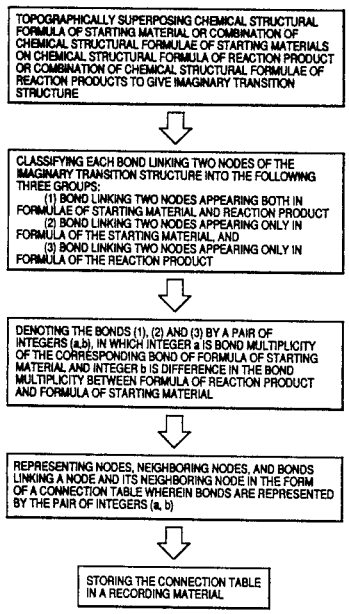

FIG. 1

TOPOGRAPHICALLY SUPERPOSING CHEMICAL STRUCTURAL FORMULA OF STARTING MATERIAL OR COMBINATION OF CHEMICAL STRUCTURAL FORMULAE OF STARTING MATERIALS ON CHEMICAL STRUCTURAL FORMULA OF REACTION PRODUCT OR COMBINATION OF CHEMICAL STRUCTURAL FORMULAE OF REACTION PRODUCTS TO GIVE IMAGINARY TRANSITION STRUCTURE

CLASSIFYING EACH BOND LINKING TWO NODES OF THE IMAGINARY TRANSITION STRUCTURE INTO THE FOLLOWING THREE GROUPS:
    (1) BOND LINKING TWO NODES APPEARING BOTH IN FORMULAE OF STARTING MATERIAL AND REACTION PRODUCT
    (2) BOND LINKING TWO NODES APPEARING ONLY IN FORMULA OF THE STARTING MATERIAL, AND
    (3) BOND LINKING TWO NODES APPEARING ONLY IN FORMULA OF THE REACTION PRODUCT

DENOTING THE BONDS (1), (2) AND (3) BY A PAIR OF INTEGERS (a,b), IN WHICH INTEGER a IS BOND MULTIPLICITY OF THE CORRESPONDING BOND OF FORMULA OF STARTING MATERIAL AND INTEGER b IS DIFFERENCE IN THE BOND MULTIPLICITY BETWEEN FORMULA OF REACTION PRODUCT AND FORMULA OF STARTING MATERIAL

REPRESENTING NODES, NEIGHBORING NODES, AND BONDS LINKING A NODE AND ITS NEIGHBORING NODE IN THE FORM OF A CONNECTION TABLE WHEREIN BONDS ARE REPRESENTED BY THE PAIR OF INTEGERS (a, b)

STORING THE CONNECTION TABLE IN A RECORDING MATERIAL

METHOD FOR PROCESSING INFORMATION ON CHEMICAL REACTIONS

This application is a continuation, of application Ser. No. 895,864, filed Aug. 12, 1986, now abandoned.

BACKGROUNDS OF THE INVENTION

1. Field of the Invention

The present invention relates to a method for processing information on chemical reactions to record and store and more particularly, to a method for processing information on changes in the chemical structures of substances concerned with chemical reactions.

2. Description of the Prior Art

Various methods for recording structural information on chemical substances, particularly organic compounds have been proposed and attempted with the development of computers in recent years. A vast amount of organic compounds and organic reactions have been studied and worked out up to the present, and it is highly required that known chemical substances or chemical reactions are retrieved in a short time, or methods for the synthesis of new substances having the desired properties are found out, by effectively utilizing information on said known compounds and reactions. For this purpose, development of a new representation mode for chemical substances and chemical reactions is needed, which can be processed by computer (that is, which can be logically judged by computer) instead of an ordinary mode such as structural formula which can be readily treated by chemists.

Typical methods for recording chemical substances (methods for the representation or description of chemical substances) are a linear notation method such as WLN (Wiswesser Linear Notation) and a method using connection table. These methods are described in, for example, W.T. Wipke, S.R. Heller, R.J. Feldmann and E. Hyde (Eds.): "Computer Representation and Manipulation of Chemical Information", John Wiley and Sons, New York, 1974. The connection table is a list in which the kind of atoms and the kinds of neighbor atoms and bonds, etc. appeared in the structural formula of chemical substance are tabulated and the connection table has an advantage that chemical substances can be retrieved atom by atom as compared with the linear notation.

Further, methods for recording information on change in the chemical structures of substances (on chemical reactions) have been proposed, but a satisfactory representation method is not developed as yet. For instance, as methods for the description of chemical reactions, there are methods using a reaction code, such as a method described in J. Valls and O. Scheiner: "Chemical Information Systems", ed. by E. Ash and E. Hyde, Ellis Horwood Limited, 1975, p. 231-248; a method described in M.A. Lobeck, Angew. Chem. Intern. Ed. Engl., 9, 578(1970); and a method described in H.J. Ziegler, J. Chem. Inf. Comput. Sci., 19, 141(1979). In these methods, a view of the representation for chemical reactions is fixed and hence, these methods have a disadvantage that any novel chemical reactions can not be described. Further, there are disadvantages that since structural information on chemical substances and information on structural changes thereof are recorded in a separate form, it is hard to make an effective information retrieval.

There are other known recording methods worked out for design of synthetic pathways of chemical substances, for instance, methods described in E.J. Corey, R.D. Cramer and W.J. Howe, J. Am. Chem. Soc., 94, 440(1972); and I. Ugi, J. Bauer, J. Braodt, J. Friedrich, J. Gasteiger, L. Jochum and W. Schubert, Angew. Chem. Intern. Ed. Engl., 18, 111(1979).

SUMMARY OF THE INVENTION

It is an object of the present invention to provide a novel method for recording and storing information on structural changes of chemical substances, and a novel method for processing the information therefor.

It is another object of the present invention to provide a method for recording and storing information on structural changes of chemical substances in a new representation mode which can be processed by computer, and a method for processing the information therefor.

It is still another object of the present invention to provide a method for recording and storing integrated information on chemical reactions including information on starting materials, products and structural changes therebetween in a new representation mode which can be processed by computer, and a method for processing the information therefor.

The present invention provides in the first aspect a method for recording and storing information on chemical reactions of producing at least one product from at least one starting material, which comprises representing the chemical reaction in such a manner that the starting material is topologically superposed upon the product, and bonds are distinguished and classified into three categories of (1) bonds linking two nodes appearing both in the starting and product stages, (2) bonds linking two nodes appearing only in the starting stage and (3) bonds linking two nodes appearing only in the product stage.

The invention also provides a method for recording and storing information on chemical reactions, which comprises:

preparing a structural diagram showing structural change of substances in the chemical reaction and/or a connection table containing information on nodes, neighboring nodes and bonds linking said two nodes in the chemical reaction, on the basis of information on bonds which are distinguished between the starting material and the product topologically superposed thereupon and classified into three categories of (1) bonds linking two nodes appearing both in the starting and product stages, (2) bonds linking two nodes appearing only in the starting stage and (3) bonds linking two nodes appearing only in the product stage, and recording and storing the chemical reaction in the form of said structural diagram and/or said connection table.

The present invention provides in the second aspect a method for processing information on chemical reactions of producing at least one product from at least one starting material, to record and store said information, which comprises:

topologically superposing the starting material upon the product on the basis of information on structures thereof, distinguishing and classifying bonds into three categories of (1) bonds linking two nodes appearing both in the starting and product stages, (2) bonds linking two nodes appearing only in the starting stage and (3) bonds linking two nodes appearing only in the product stage, and preparing a structural diagram showing structural change of substances in the chemical reaction and/or a connection table containing information on nodes, neighboring nodes and bonds linking said two nodes in the chemical reaction.

It is further object of the present invention to provide a novel method for processing information on chemical substances on basis of the information on chemical reactions to record and store said information.

It is furthermore object of the present invention to provide a method for processing information on chemical substances on the basis of the information on chemical reactions to record and store said information in a new representation mode which can be processed by computer.

The present invention provides in the third aspect:

[I] a method for processing information on chemical reactions of producing at least one product from at least one starting material, said information being given in the form of imaginary transition structures in which the starting material is topologically superposed upon the product and bonds are distinguished and classified into three categories of (1) bonds linking two nodes appearing both in the starting and product stages, (2) bonds linking two nodes appearing only in the starting stage and (3) bonds linking two nodes appearing only in the product stage,
which comprises deleting said bonds (3) appearing only in the product stage from the imaginary transition structure to obtain a structure of the starting material;

[II] a method for processing information on chemical reactions, said information being given in the form of the above-mentioned imaginary transition structures, which comprises deleting said bonds (2) appearing only in the starting stage from the imaginary transition structure to obtain a structure of the product;

[III] a method for processing information on chemical reactions, said information being given in the form of the above-mentioned imaginary transition structures, which comprises:
(i) deleting said bonds (3) appearing only in the product stage from the imaginary transition structure to obtain a structure of the starting material,
(ii) deleting said bonds (2) appearing only in the starting stage from the imaginary transition structure to obtain a structure of the product material, and
(iii) recording said structures of the starting material and the product on the same recording material or displaying them on the same screen of a display device;

[IV] a method for processing information on chemical reactions, said information being given in the form of connection tables containing information on nodes and bonds linking two nodes which are distinguished between the starting material and the product topologically superposed thereon and classified into three categories of (1) bonds linking two nodes appearing both in the starting and product stages, (2) bonds linking two nodes appearing only in the starting stage and (3) bonds linking two nodes appearing only in the product stage,
which comprises deleting said bonds (3) appearing only in the product stage from the connection table to obtain a connection table of the starting material; and

[V] a method for processing information on chemical reactions, said information being given in the form of the above-mentioned connection tables, which comprises deleting said bonds (2) appearing only in the starting stage from the connection table to obtain a connection table of the product.

According to the present invention, a chemical reaction can be basically described by a simple representation of nodes comprising atoms, groups, etc. and bonds linking two adjacent nodes. The bonds linking two nodes in the reaction system are distinguished and classified into three categories, i.e., bonds appearing only in the starting stage, bonds appearing only in the product stage and bonds appearing both in the starting and product stages, and hence, not only the chemical reaction but also substances such as starting materials and products concerned with the chemical reaction can be simultaneously described. The method of the present invention is excellent in recording and storing information on chemical substances as well as chemical reactions, as compared with the conventional description methods.

In the first, the employment of the representation mode according to the present invention in recording and storing information on a chemical reaction makes information processing by computer easy and does not make storage capacity large. Further, the employment of this representation mode makes simple an entry of the chemical reaction in a computer. Hence, the storing and the management of information in a recording medium can be easily conducted.

Information on a chemical reaction can be stored (entered) in a computer as a two-dimensional or three-dimensional structural diagram (graph) and/or connection table according thereto. The term "structural diagram (graph)" used herein means a diagram [referred to as "imaginary transition structure" (ITS)] which represents the changes in the chemical structures of substances related to a given chemical reaction with the abovementioned representation mode. By using this structural diagram, the chemical reaction can be described by a form which is visually acceptable and readily comprehensible to chemists and technologists in accordance with the ordinary structural formula of chemical substance or the three-dimensional form thereof. The term "connection table of ITS" (hereinafter simply referred to as "connection table") means a table which essentially consists of a combination of the kind of nodes and the kinds of neighboring nodes and bonds linking these two nodes, being simple and understandable. By using this connection table, information on the chemical reaction can be stored in a recording medium without requiring so large capacity.

In any form of the structural diagram and the connection table, bonds linking two adjacent nodes are represented in relation to the starting stage and the product stage, so that the structural diagram and the connection table integratedly contain information on substances relating to the chemical reaction in addition to the chemical reaction. Accordingly, this representation mode has great advantages in that information on chemical reactions and substances can be simultaneously recorded and stored, as compared with the conventional modes and in that the retrieval and the collation of chemical reactions and substances can be made atom by atom utilizing the registered structural diagrams and/or connection tables.

Further, when the connection table contains information on the space coordinate of each node, the structural diagram and the connection table can be transformed into each other and a chemical reaction can be represented by any form.

In addition to the above-described advantages, not only individual reactions but also a plurality of consecutive reactions (multi-step reactions) can be tabulated by a table, when the bond linking two nodes is denoted by a pair of integers (a,b), wherein the integer a is bond multiplicity of the corresponding bond of the starting material and the integer b is difference in the bond multiplicity between the product and the starting material. Using this notation, an arbitrary intermediate reaction or a series of synthesis reactions can be simply represented.

In the second, according to the present invention, information on a chemical reaction can be automatically obtained in the form of a structural diagram of two-dimension or three-dimension and/or a connection table, also on the basis of information on the starting material and the product concerned therewith. More in detail, only by processing information on chemical substances comprising the starting material and the product, systematic information on the chemical reaction to which they are related can be obtained. The obtained reaction information can be directly recorded and stored in a computer.

In the third, according to the present invention, information on chemical substances concerned with a chemical reaction can be automatically and independently obtained by manipulating information on chemical reactions which are registered in the form of an imaginary transition structure (ITS) and/or a connection table of ITS in a computer, on the contrary. More in detail, the reaction information can be transformed to the substance information by subjecting the ITS or the connection table of the chemical reaction to a simple graphic processing or to a simple operation processing, depending upon the distinction of bonds applied thereto. Hence, the substance information contained in the ITS or the connection tables of chemical reactions is separated from the reaction information and the utilization thereof becomes easier and increased.

When the substance information is obtained in the form of a structural formula (i.e., in a two-dimensional form) or in a three-dimensional form, there are advantages that the obtained information is visually acceptable and can be directly used in the practical field because the obtained form is almost the same as the ordinary representation form of chemical substances. When the substance information is obtained in the form of a connection table, there are other advantages that the comparison and collation with the reaction information represented in the same form is easy and the obtained information can be stored in a computer without a large capacity. The grahic forms and/or the connection tables of substances may be stored in a computer, recorded on a paper, or displayed on a screen such as CRT.

Further, the arbitary transformation between the grahic form and the connection table is also possible to denote the chemical substance in any form thereof, when the connection table contains information on space coordinate of each node. By using the registered grahic form and/or the connection table, chemical substances can be retrieved and collated atom by atom. Especially, the registration of the substance information in the form of the connection table (or both of the connection table and the grahic form) makes information processing by computer easy and makes the registaration itself in a computer simple, so that the storing and the management of the substance information can be readily conducted.

Therefore, the information retrieval of chemical reactions and chemical substances concerned therewith can be made effectively and in a short time on the basis of the stored reaction information, or on the basis of both the stored reaction information and the stored substance information, so that the time required for the collection of information on studies and investigations can be shortened, the amount of information can be increased and researches can be efficiently made.

The method of the present invention can be effectively applied to the fields of structural analysis of chemical substances, molecular modeling and heuristic analysis of organic synthesis, all of which are highly demanded by workers concerned with the manufacture of medicines. Further, retrieval of substructures of chemical substances and chemical reactions, correlation between structure and activity, design of synthetic pathways, automatic determination of the chemical structure of unknown compounds, mechanistic evaluation for the reaction of complicated compounds under certain conditions and prediction of mechanism therefore can be made within a practically possible range in a short time.

BRIEF DESCRIPTION OF THE DRAWING

FIG. 1 illustrates a flow sheet for performing the method of the present invention.

DETAILED DESCRIPTION OF THE INVENTION

The present invention can be implemented by employing a conventional computer as well as a conventional recording apparatus and a conventional output apparatus. FIGS. 1 and 2 are given to show representative recording and output systems, respectively, employable for carrying out the method of the invention.

According to the recording system illustrated in FIG. 1, a description of a chemical reaction which is input from Terminal is schematically reproduced in the form of ITS in the ITS-Drawing Module, and a connection table is produced in the ITS-Connection Table Generating Module. According to the prepared ITS, bond perception, atom perception and coordinate generation are performed, respectively, in the bond-perception module (and the complex-bond-number generator), the atom-perception module and the coordinate generating module (and the stereo perception module). The results are stored in the ITS-CT File and can be reproduced on another terminal using the Colored-Bond Display Module.

According to the output system illustrated in FIG. 2, a structural formula of the starting material and a structural formula of the product are reproduced in the PS (projection to starting stage) Module (and Complex-Bond-Number Transformer) and the PP (projection to product stage) Module (and Complex-Bond-Number Transformer), respectively, based on the connection table obtained from ITS-CT File. The reproduced structural formulae are stored in the Structure CT File and output through the terminal.

In the present invention, the structural change of the chemical substances through a chemical reaction is described by superposing topologically the starting material and the product and classifying bonds into three categories, i.e., bonds appearing only in the starting stage, bonds appearing only in the product stage and bonds appearing both in the starting and product stages.

Now, the method for recording and storing information on chemical reactions according to the present invention will be described by referring to the hydrolysis of ethyl acetate catalyzed by hydrochloric acid. The chemical reaction can be represented by the following equation:

CH₃COOCH₂CH₃+H₂O+HCL→CH-
₃COOH+CH₃CH₃CH₂OH+HCL     (Eq. 1)

Nodes for all of starting materials concerned with the reaction (which constitute the starting stage) are numbered as follows.

STARTING STAGE

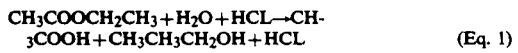

The starting stage (starting material group) represented by the ordinary structural formulae is superposed topologically (i.e., in the same phase) upon the product stage (product group), to obtain the following structural diagram:

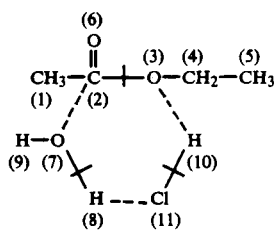
(ITS 1)

wherein
 (i) the symbol —indicates bonds appearing both in the starting and product stage,
 (ii) the symbol —+— indicates bonds appearing only in the starting stage, and
 (iii) the symbol ···· indicates bonds appearing only in the product stage.

In the present invention, the above structural diagram is referred to as imaginary transition structure (abbreviated as ITS). Namely, the ITS is a diagram of two-dimension or three-dimension where bonds linking two adjacent nodes are distinguished between the starting materials and the products topologically superposed thereon and classified into said three categories (i) to (iii).

The product stage obtained by the hydrolysis reaction is represented by the following formulae in which node's number corresponds to that of the starting stage.

PRODUCT STAGE

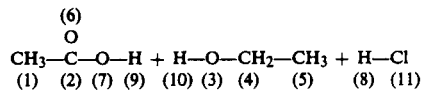

Namely, the term "topologically superpose" used herein means that the chemical structures of the starting materials are combined with those of the products in such a manner that the nodes appearing in the former coincide with those appearing in the latter.

In the present invention, nodes of the substances concerned with a chemical reaction are allowed to be individual atoms contained in the starting and product stages, or groups such as functional groups, for example, methyl group (nodes 1 and 5), methylene group (node 4), etc. Part of nodes appearing in the starting and product stages may be omitted in representing the chemical reaction, and the invention is not restricted by the way of decision of nodes.

In the imaginary transition structure (ITS) according to the present invention, the notation for distinguishing the three kinds of bonds is by no means limited to the symbols defined by the above (i) to (iii), but the notation may be done by any means, for example: characters such as numerals (1, 2, 3,·····, colors (black, red, green, etc.), so long as users can judge the notation through the senses and it can be processed by computer.

In the invention hereinafter,
 (i) bonds (symbol —) appearing both in the starting and product stages are referred to as colorless bonds or "par-bonds",
 (ii) bonds (symbol —+—) appearing only in the starting stage are referred to as "out-bonds", and
 (iii) bonds (symbol ····) appearing only in the product stage are referred to as "in-bonds".

Further, the out- and in-bonds are together referred to as colored bond and all the bonds appeared in ITS (par-, out- and in-bonds) are referred to as "ITS bonds" or imaginary bonds.

The types of bonds appearing in the imaginary transition structure are shown in Table 1, wherein the numerical value in the horizontal means a characteristic of in-and-out.

TABLE 1

| Characteristic of In-and-out | −3 | −2 | −1 | 0 | +1 | +2 | +3 |
|---|---|---|---|---|---|---|---|
| Single Bond | | | —+— (1−1) | — (1+0) | ---- (0+1) | | |
| Double Bond | | ≠ (2−2) | ≠ (2−1) | = (2+0) | ==== (1+1) | ==== (0+2) | |
| Triple Bond | ≢ (3−3) | ≢ (3−2) | ≡ (3−1) | ≡ (3+0) | ≡ (2+1) | ==== (1+2) | ===== (0+3) |

In Table 1, a bond represented by the symbol — is a single in-bond and denoted by a pair of integers (0+1) where 0 indicates that no bond is in the starting stage before reaction and +1 indicates that a bond is singly formed in the product stage after reaction. Similarly, a bond represented by the symbol —+— is a single out-bond and denoted by a pair of integers (1—1), which means that a single bond in the starting stage before reaction is cleaved (to disappear) in the product stage after reaction. A bond represented by a pair of integers (2-1) is a double bond singly cleaved and denoted by the symbol ±.

In this way, the kinds of bonds can be denoted by a pair of integers (a,b) wherein the integer a is bond multiplicity of the corresponding bond of the starting material and the integer b is difference in the bond multiplicity between the product and the starting material, which is referred to as "complex bond number" or "imaginary multiplicity". Even when the bond multiplicity is two or more, it can be simply denoted. If desired, the comma (,) of (a,b) may be deleted. This notation does not need large storage capacity and can be directly processed by computer, so that the notation is particularly preferred in the storage of data on chemical reactions and suitably employed in preparing a connection table described below.

In the second place, the method for processing information on chemical reactions to record and store according to the present invention will be described.

Individual reactions are recorded and stored (registered) in the following manner by using the above-described representation mode viewed from bonds linking two adjacent nodes. The recording and storing of chemical reactions is made in the form of the imaginary transition structure, the connection table or a combination thereof.

Referring to the hydrolysis of ethyl acetate catalyzed by hydrochloric acid (Eq. 1), a two-dimensional imaginary transition structure such as shown in ITS 1 is prepared on the basis of input information on bonds wherein the kinds of the nodes (1) to (11) and the bonds linking two nodes are distinguished from one another by means of colorless or colored bond and in- or out-bond. It is also possible to prepare a three-dimensional imaginary transition structure. In this case, the information on the bonds needs to contain information on relative space conformation (two-dimensional or three-dimensional coordinate) of each node.

Alternatively, the imaginary transition structure of the hydrolysis reaction can be prepared on the basis of input information on chemical structures of the starting materials and the products. In this processing method, the inputted structures of the starting materials are topologically superposed upon those of the products and then the bonds are distinguished and classified into the above three kinds of bonds, whereby the structural changes of substances in the reaction are represented by the ITS.

More in detail, all the starting materials and the products are represented by the ordinary structural formulae, and nodes are respectively decided on the formulae and consecutively numbered, in correspondence between the starting materials and the products. Namely, the above-shown Starting Stage and Product Stage are input in a computer. In the information processing, the information on structures of substances can be input in the form of a figure which is easy to be treated by technologists such as the structural formula (two-dimensional form) or a three-dimensional form. The information on the substances may be input one by one in an interactive mode as character information, for example, "node (1) and node (2) are linked by a bond having a multiplicity of 1". In the case of the input by character, symbol, etc., the locational information such as two-dimensional or three-dimensional coordinates of nodes can be also input. Then the starting stage and the product stage are topologically superposed, namely in the manner that the nodes are coincident therebetween to obtain the following diagram:

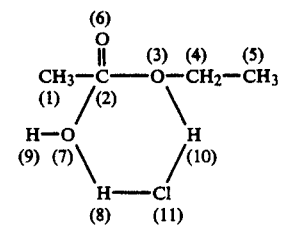

Subsequently, the bonds appearing in the obtained diagram are distinguished by the above three kinds of bonds and denoted by the symbol —, —+— or ···· to obtain an imaginary transition structure of ITS 1.

The individual reactions are entered (registered) in a computer in the form of the resulting two-dimensional or three-dimensional imaginary transition structure (diagram). This entry form is very excellent in that it is in a form similar to the structural formula or the three-dimensional form which can be visually acceptable and immediately understandable to chemists who intend to utilize information on chemical reactions.

Further, various information related to chemical reactions can be tuned and obtained by manipulating the entered reaction information, to be applied to the retrieval and the collation of chemical reactions and substances. For instance, the information on chemical structure of substances concerned with reactions are obtained by deleting specific bonds from the imaginary transition structure, as described later. This means that the imaginary transition structure according to the invention contains information not only on the chemical reactions but also on the chemical substances and that it is possible to carry out the retrieval of compounds as well as that of reactions by use of this entry mode.

Through another manipulation, that is, deleting only the colorless bonds (par-bonds) from ITS 1, there can be obtained a structure in which nodes are connected with alternate in-bonds and out-bonds: [(2)−(3)+(10)−(11)+(8)−(7)+(2)], wherein the signs − and + represent an out-bond and an in-bond, respectively. This is referred to as "reaction string". The reaction string derived from an ITS has a diagram (pattern) inherent to a reaction type. The above reaction string is a diagram inherent to the hydrolysis of the ester. Namely, it is possible to independently extract a reaction string which is characteristic representation for every reaction type, whereby the retrieval of chemical reactions will become further easy. It is also possible to extract a ring structure (ring opening, ring closing, etc.) concerned with a chemical reaction.

A connection table containing information on nodes, neighbor nodes and bonds linking said two nodes according to ITS for the hydrolysis reaction of ester (Eq. 1) is prepared on the basis of input information on the kinds of the nodes (1) to (11) and the bonds which are distinguished by means of colorless or colored bond and in- or out-bond.

The connection table is also prepared on the basis of the aforementioned input information on the starting materials and the products. The structures of the starting materials are topologically superposed upon those of the products, the bonds are distinguished and classified into the above three kinds of bonds, and then the nodes, the neighbor nodes, the bonds linking two nodes and if desired, the coordinates of nodes are represented by numeral, character, etc. to list up them. In this processing, "topologically superpose" means that the corresponding bonds are compared and collated between the structures of the starting materials and those of the products as well as that both the structures are graphically superposed in such a manner that the nodes are coincident with each other.

Table 2 shows the resulting connection table. The connection table also contains information on two-dimensional coordinate (xy-coordinate) of each node.

TABLE 2

| Node | | Coordinate | | Neighbor 1 | Neighbor 2 | Neighbor 3 | Neighbor 4 |
|---|---|---|---|---|---|---|---|
| No. | Kind | X | Y | Node (a, b) | Node (a, b) | Node (a, b) | Node (a, b) |
| 1 | $CH_3$ | 0 | 0 | 2 (1 + 0) | | | |
| 2 | C | 200 | 0 | 1 (1 + 0) | 3 (1 − 1) | 6 (2 + 0) | 7 (0 + 1) |
| 3 | O | 400 | 0 | 2 (1 − 1) | 4 (1 + 0) | 10 (0 + 1) | |
| 4 | $CH_2$ | 600 | 0 | 3 (1 + 0) | 5 (1 + 0) | | |
| 5 | $CH_3$ | 800 | 0 | 4 (1 + 0) | | | |
| 6 | O | 200 | 200 | 2 (2 + 0) | | | |
| 7 | O | 200 | −200 | 2 (0 + 1) | 8 (1 − 1) | 9 (1 + 0) | |
| 8 | H | 341 | −341 | 7 (1 − 1) | 11 (0 + 1) | | |
| 9 | H | 59 | −341 | 7 (1 + 0) | | | |
| 10 | H | 541 | −141 | 3 (0 + 1) | 11 (1 − 1) | | |
| 11 | Cl | 541 | −341 | 8 (0 + 1) | 10 (1 − 1) | | |

As shown in Table 2, the connection table is a table in which all nodes, two-dimensional coordinates thereof (node 1 being the orgin), all nodes neighboring on each node and the kinds of bonds linking two adjacent nodes are listed in order of node's number with respect to the starting stage (ethyl acetate, water and hydrochloric acid) and the product stage (acetic acid, ethanol and hydrochloric acid) concerned with the reaction.

Alternatively, the connection table may be prepared on the basis of the resulting imaginary transition structure, or it can be also prepared with information which is input directly in the form of an imaginary transition structure.

Subsequently, individual reactions in the form of the connection table are entered in a computer. This entry form is superior in that it does not require large storage capacity and can be directly processed by the computer. It is possible to enter a combination of the connection table and the imaginary transition structure in the computer as a preferred embodiment of the present invention.

The information on the space coordinates of nodes may be incorporated in the connection table as described above. Further, information on stereochemistry and electric charges of nodes; information on spectral and physical properties of substances related to chemical reactions; and information on reaction enthalpy, reaction temperature, reaction time, catalysts, reaction atmosphere, reaction media, yields, by-products, etc. may be combined to the imaginary transition structure and/or the connection table, if desired. When the imaginary transition structure or the connection table entered in the computer contains these additional information, the imaginary transition structure or the connection table can be widely used as data base in the fields of structure search systems, reaction search systems and design of organic synthesis pathways.

In entering (registering) said imaginary transition structures and/or connection tables in a computer, they may be numbered one by one or reaction names may be registered together with them in order to facilitate the storage, management and retrieval of the reaction information.

It is possible to denote starting materials, products and reaction formula on the basis of the registered connection table and to extract a reaction string and a ring structure therefrom. Further, it is possible that multi-step reactions are integrated to be denoted by a single connection table by subjecting bonds represented by the pair of integers (a,b) to appropriate operation processing. That is, not only individual reactions but also the whole of complicated reactions such as those in the synthesis of organic compounds can be simply denoted and a part of these reactions can be extracted therefrom and denoted.

Accordingly, the registered connection table can be utilized as the optimum entry form in the various fields of chemistry to which the computer is applicable, i.e., the molecular modeling according to the specific properties of substances, the design of synthetic pathways of organic compounds and the determination of structures of unknown compounds.

It is also possible that the imaginary transition structure is prepared on the basis of the registered connection table and that the connection tables and the imaginary transition structures for chemical reactions are transformed into each other in the above-described various search systems. This arbitrary transformation brings about the enhancement in the all-around application of the search system and the usefullness thereof.

The entry of the imaginary transition structure and/or the connection table in a computer may be done by storing them in main storage thereof or in an appropriate recording medium (magnetic disk, optical disk or magnetic tape).

The registered imaginary transition structure and/or the connection table can be recorded on a recording material such as plain paper by an appropriate recording device, or can be displayed on a colored CRT connected to the computer or electronic equipment.

In the third place, the method for processing information on chemical reactions to record and store information on chemical substances according to the present invention will be described by referring to the hydrolysis of ethyl acetate catalyzed by hydrochloric acid represented by Eq. 1.

The information on substances concerned with chemical reactions can be obtained in a graphic form and/or in the form a connection table by manipulating the reaction information in an entry mode of the imaginary transition structure and/or the connection table of ITS. More in detail, the structural information on substances comprising the starting materials and the products of reactions is independently obtained by subjecting the ITS and/or the ITS connection table to an operation of deleting specific bonds therefrom in the following manner.

All the in-bonds with the symbol are deleted from the imaginary transition structure of the hydrolysis reaction represented by ITS 1, that is, the in-bonds are changed to non-bonds. The remaining par-bonds with the symbol — and out-bonds with the symbol are denoted by the ordinary bond notation according to the bond multiplicities thereof to obtain structural formulae of the starting stage. This operation is called as "projection to starting stage" (abbreviated by PS).

On the other hand, the structural formulae of the product stage are obtained by deleting all the out-bonds from ITS 1, namely by changing the out-bonds to non-bonds and then changing the remaining par-bonds and in-bonds to the ordinary bond notation according to the bond multiplicities thereof. This operation is called as "projection to product stage" (abbreviated by PP).

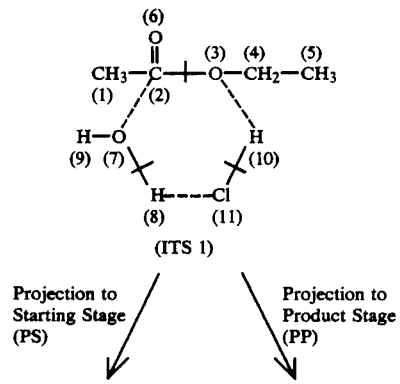

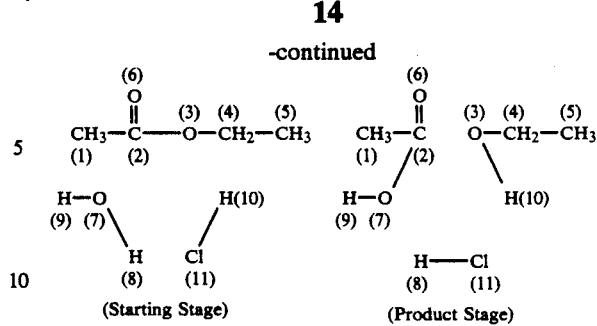

When the ITS is a three-dimensional ITS, the starting materials and the products are obtained in a three-dimensional form through the PS and PP modules.

Thus, the substance information is obtained in the form of a diagram (a structural formula or a three-dimensional form) which is usually treated by the technologists by processing information based on the ITS according to the present invention, and the user can understand visually and immediately.

The information on the starting materials and the products concerned with chemical reactions can be also derived from the entered ITS connection tables for reactions. For instance, when the bonds linking two nodes in the hydrolysis reaction are denoted by the pair of integers (a,b) as shown in Table 2, the operation for the projection to the starting stage (PS) can be made by changing the notation of (a,b) to notation of (a) and preparing a new connection table based on this notation. The PS operation is by no means limited to one using the notation of (a) and may be made by using another notation capable of denoting information equivalent thereto, namely appearance or not of a bond linking two nodes and bond multiplicity.

The operation for the projection to the product stage (PP) is made as follows: An addition operation is made for (a,b).

$$a+b=c$$

The resulting value c indicates a bond multiplicity in the product stage after reaction. The notation of (c) takes place of the notation of (a,b) for each bond and a new connection table is prepared. The PP operation is either by no means limited to one using the notation of (c) and may be made by using another notation capable of denoting information equivalent thereto.

Tables 3 and 4 show the resulting connection tables of the starting materials and the products, respectively. Each connection table contains information on two-dimensional coordinates (xy-coordinates) of nodes.

TABLE 3

| Node | | Coordinate | | Neighbor 1 | Neighbor 2 | Neighbor 3 | Neighbor 4 |
|---|---|---|---|---|---|---|---|
| No. | Kind | X | Y | Node (a) | Node (a) | Node (a) | Node (a) |
| 1 | CH$_3$ | 0 | 0 | 2 (1) | | | |
| 2 | C | 200 | 0 | 1 (1) | 3 (1) | 6 (2) | |
| 3 | O | 400 | 0 | 2 (1) | 4 (1) | | |
| 4 | CH$_2$ | 600 | 0 | 3 (1) | 5 (1) | | |
| 5 | CH$_3$ | 800 | 0 | 4 (1) | | | |
| 6 | O | 200 | 200 | 2 (2) | | | |
| 7 | O | 200 | −200 | 8 (1) | 9 (1) | | |
| 8 | H | 341 | −341 | 7 (1) | | | |
| 9 | H | 59 | −341 | 7 (1) | | | |
| 10 | H | 541 | −141 | 11 (1) | | | |
| 11 | Cl | 541 | −341 | 10 (1) | | | |

TABLE 4

| Node | | Coordinate | | Neighbor 1 | Neighbor 2 | Neighbor 3 | Neighbor 4 |
|---|---|---|---|---|---|---|---|
| No. | Kind | X | Y | Node (c) | Node (c) | Node (c) | Node (c) |
| 1 | $CH_3$ | 0 | 0 | 2 (1) | | | |
| 2 | C | 200 | 0 | 1 (1) | 6 (2) | 7 (1) | |
| 6 | O | 200 | 200 | 2 (2) | | | |
| 7 | O | 200 | −200 | 2 (1) | 9 (1) | | |
| 9 | H | 59 | −341 | 7 (1) | | | |
| 3 | O | 400 | 0 | 4 (1) | 10 (1) | | |
| 4 | $CH_2$ | 600 | 0 | 3 (1) | 5 (1) | | |
| 5 | $CH_3$ | 800 | 0 | 4 (1) | | | |
| 10 | H | 541 | −141 | 3 (1) | | | |
| 8 | H | 341 | −341 | 11 (1) | | | |
| 11 | Cl | 541 | −341 | 8 (1) | | | |

The manipulation of the reaction imformation by use of the connection tables makes it possible to directly process by computer and to simply output information on a specific substance in a short time. The recording and storing of the substance information with the connection tables does not need large capacity.

The substance information can be arbitrarily transformed between the graphic form and the connection table, which is similar to the relationship between the imaginary transition structure of a reaction and the ITS connection table. For example, the connection table of a reaction is subjected to the PS or PP module and the obtained connection table of substances is transformed into the graphic form to obtain the starting materials or the products.

Thus obtained graphic form and/or the connection table for substances related to chemical reactions may be independently stored(entered) in a computer, or may be recorded or displayed by use of an appropriate means in the same manner as afore-described. The entry and recording of the substance information may be done in a combination of the graphic form and the connection table. Alternatively, the starting material and the product may be recorded or displayed in a graphic form together with the chemical reaction, or with further ITS.

The above-shown information on space coordinates of nodes, the information on stereochemistry and electronic charges of nodes; information on spectral and physical properties of substances; and information on name, conditions, yields and by-products of the reaction related to said substances; etc. may be incorporated in the graphic form and/or the connection table, if desired. When the substance information stored in the computer contains these additional information, the information can be widely used as data base in the fields of structure search systems, reaction search systems and design of organic synthesis pathways. Further, when the synthesis reaction is composed of multi-step reactions, an intermediate material (main product) and by-product produced by the reaction at each step can be denoted. In entering said graphic forms and/or connection tables in a computer, they may be numbered one by one or entered with the name thereof, to facilitate the storage, management and retrieval of the substance information.

Furthermore, the use of a combination of the reaction information with the substance information can bring about the further application to the chemical field utilizing computer such as molecular modeling according to the specific properties of substances, the design of synthetic pathways of organic compounds and the determination of the structures of unknown compounds.

The following examples will further illustrate the method for recording and storing information on chemical reactions according to the present invention.

EXAMPLE 1

Reaction for addition of n-butyl lithium to acetone

The reaction is represented by the schematic equation.

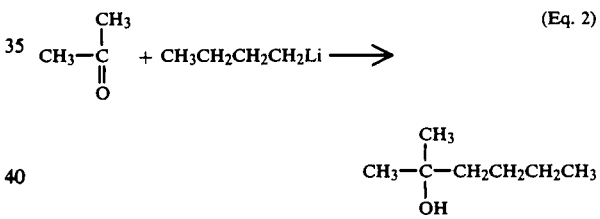
(Eq. 2)

The addition reaction is denoted by an imaginary transition structure.

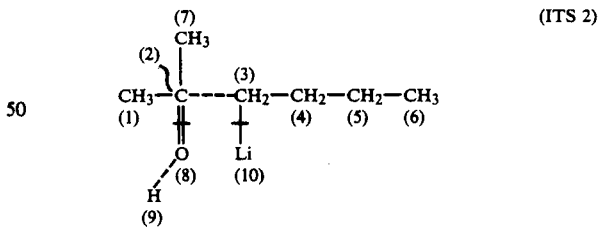
(ITS 2)

A connection table corresponding to ITS 2 was prepared. The connection table is set forth in Table 5, which includes information on two-dimensional coordinate (xy-coordinate) of each node.

TABLE 5

| Node | | Coordinate | | Neighbor 1 | Neighbor 2 | Neighbor 3 | Neighbor 4 |
|---|---|---|---|---|---|---|---|
| No. | Kind | X | Y | Node (a, b) | Node (a, b) | Node (a, b) | Node (a, b) |
| 1 | $CH_3$ | 0 | 0 | 2 (1 + 0) | | | |
| 2 | C | 200 | 0 | 1 (1 + 0) | 3 (0 + 1) | 7 (1 + 0) | 8 (2 − 1) |
| 3 | $CH_2$ | 400 | 0 | 2 (0 + 1) | 4 (1 + 0) | 10 (1 − 1) | |
| 4 | $CH_2$ | 600 | 0 | 3 (1 + 0) | 5 (1 + 0) | | |
| 5 | $CH_2$ | 800 | 0 | 4 (1 + 0) | 6 (1 + 0) | | |
| 6 | $CH_3$ | 1000 | 0 | 5 (1 + 0) | | | |

TABLE 5-continued

| Node | | Coordinate | | Neighbor 1 | Neighbor 2 | Neighbor 3 | Neighbor 4 |
|---|---|---|---|---|---|---|---|
| No. | Kind | X | Y | Node (a, b) | Node (a, b) | Node (a, b) | Node (a, b) |
| 7 | CH$_3$ | 200 | 200 | 2 (1 + 0) | | | |
| 8 | O | 200 | −200 | 2 (2 − 1) | 9 (0 + 1) | | |
| 9 | H | 59 | −341 | 8 (0 + 1) | | | |
| 10 | Li | 400 | −200 | 3 (1 − 1) | | | |

Then, ITS 2 was subjected to PS module and PP module to obtain structural formulae of the starting stage and the product stage, respectively.

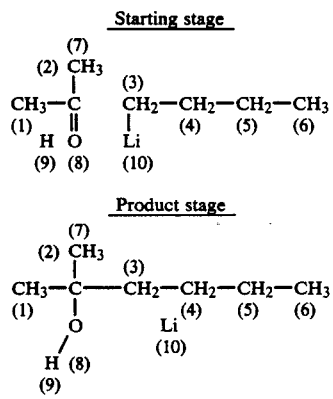

The connection table was also subjected to PS module and PP module to obtain connection tables for the starting stage and the product stage. The results are respectively set forth in Tables 6 and 7.

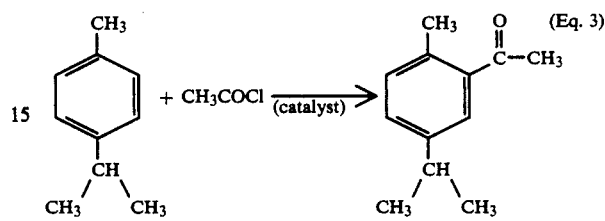  (Eq. 3)

An imaginary transition structure (ITS 3) for the Friedel-Crafts reaction and structural formulae of the starting stage and the product stage, which were obtained by subjecting ITS 3 to PS module and PP module, are represented as follows.

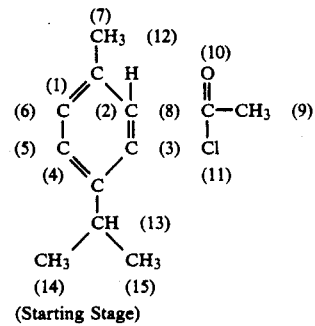

(Starting Stage)

TABLE 6

| Node | | Coordinate | | Neighbor 1 | Neighbor 2 | Neighbor 3 | Neighbor 4 |
|---|---|---|---|---|---|---|---|
| No. | Kind | X | Y | Node (a) | Node (a) | Node (a) | Node (a) |
| 1 | CH$_3$ | 0 | 0 | 2 (1) | | | |
| 2 | C | 200 | 0 | 1 (1) | 7 (1) | 8 (2) | |
| 7 | CH$_3$ | 200 | 200 | 2 (1) | | | |
| 8 | O | 200 | −200 | 2 (2) | | | |
| 3 | CH$_2$ | 400 | 0 | 4 (1) | 10 (1) | | |
| 4 | CH$_2$ | 600 | 0 | 3 (1) | 5 (1) | | |
| 5 | CH$_2$ | 800 | 0 | 4 (1) | 6 (1) | | |
| 6 | CH$_3$ | 1000 | 0 | 5 (1) | | | |
| 10 | Li | 400 | −200 | 3 (1) | | | |
| 9 | H | 59 | −341 | | | | |

TABLE 7

| Node | | Coordinate | | Neighbor 1 | Neighbor 2 | Neighbor 3 | Neighbor 4 |
|---|---|---|---|---|---|---|---|
| No. | Kind | X | Y | Node (c) | Node (c) | Node (c) | Node (c) |
| 1 | CH$_3$ | 0 | 0 | 2 (1) | | | |
| 2 | C | 200 | 0 | 1 (1) | 3 (1) | 7 (1) | 8 (1) |
| 3 | CH$_2$ | 400 | 0 | 2 (1) | 4 (1) | | |
| 4 | CH$_2$ | 600 | 0 | 3 (1) | 5 (1) | | |
| 5 | CH$_2$ | 800 | 0 | 4 (1) | 6 (1) | | |
| 6 | CH$_3$ | 1000 | 0 | 5 (1) | | | |
| 7 | CH$_3$ | 200 | 200 | 2 (1) | | | |
| 8 | O | 200 | −200 | 2 (1) | 9 (1) | | |
| 9 | H | 59 | −341 | 8 (1) | | | |
| 10 | Li | 400 | −200 | | | | |

EXAMPLE 2

Acylation reaction by Friedel-Crafts reaction

The reaction is represented by the schematic equation.

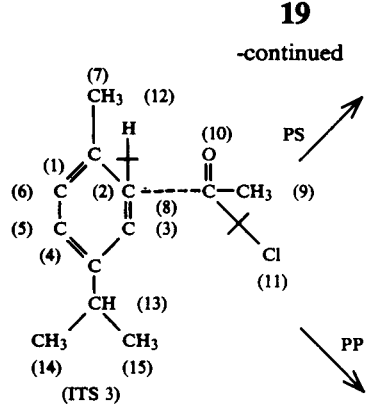

(ITS 3)

-continued

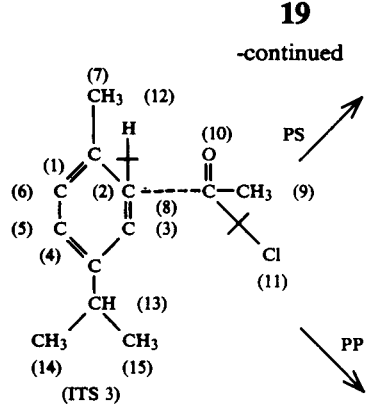

(Product Stage)

A connection table corresponding to ITS 3 was prepared. The connection table is set forth in Table 8, which includes information on the two-dimensional coordinate (xy-coordinate) of each node. Further, the connection table was subjected to PS module and PP module to obtain connection tables for the starting stage and the product stage. The results are respectively set forth in Tables 9 and 10.

TABLE 8

| Node | | Coordinate | | Neighbor 1 | Neighbor 2 | Neighbor 3 | Neighbor 4 |
|---|---|---|---|---|---|---|---|
| No. | Kind | X | Y | Node (a, b) | Node (a, b) | Node (a, b) | Node (a, b) |
| 1 | C | 0 | 200 | 2 (1 + 0) | 6 (2 + 0) | 7 (1 + 0) | |
| 2 | C | 173 | 100 | 1 (1 + 0) | 3 (2 + 0) | 8 (0 + 1) | 12 (1 − 1) |
| 3 | C | 173 | −100 | 2 (2 + 0) | 4 (1 + 0) | | |
| 4 | C | 0 | −200 | 3 (1 + 0) | 5 (2 + 0) | 13 (1 + 0) | |
| 5 | C | −173 | −100 | 4 (2 + 0) | 6 (1 + 0) | | |
| 6 | C | −173 | 100 | 1 (2 + 0) | 5 (1 + 0) | | |
| 7 | CH₃ | 0 | 400 | 1 (1 + 0) | | | |
| 8 | C | 373 | 100 | 2 (0 + 1) | 9 (1 + 0) | 10 (2 + 0) | 11 (1 − 1) |
| 9 | CH₃ | 573 | 100 | 8 (1 + 0) | | | |
| 10 | O | 373 | 300 | 8 (2 + 0) | | | |
| 11 | Cl | 373 | −100 | 8 (1 − 1) | | | |
| 12 | H | 273 | 273 | 2 (1 − 1) | | | |
| 13 | CH | 0 | −400 | 4 (1 + 0) | 14 (1 + 0) | 15 (1 + 0) | |
| 14 | CH₃ | −100 | −573 | 13 (1 + 0) | | | |
| 15 | CH₃ | 100 | −573 | 13 (1 + 0) | | | |

TABLE 9

| Node | | Coordinate | | Neighbor 1 | Neighbor 2 | Neighbor 3 | Neighbor 4 |
|---|---|---|---|---|---|---|---|
| No. | Kind | X | Y | Node (a) | Node (a) | Node (a) | Node (a) |
| 1 | C | 0 | 200 | 2 (1) | 6 (2) | 7 (1) | |
| 2 | C | 173 | 100 | 1 (1) | 3 (2) | 12 (1) | |
| 3 | C | 173 | −100 | 2 (2) | 4 (1) | | |
| 4 | C | 0 | −200 | 3 (1) | 5 (2) | 13 (1) | |
| 5 | C | −173 | −100 | 4 (2) | 6 (1) | | |
| 6 | C | −173 | 100 | 1 (2) | 5 (1) | | |
| 7 | CH₃ | 0 | 400 | 1 (1) | | | |
| 12 | H | 273 | 273 | 2 (1) | | | |
| 13 | CH | 0 | −400 | 4 (1) | 14 (1) | 15 (1) | |
| 14 | CH₃ | −100 | −573 | 13 (1) | | | |
| 15 | CH₃ | 100 | −573 | 13 (1) | | | |
| 8 | C | 373 | 100 | 9 (1) | 10 (2) | 11 (1) | |
| 9 | CH₃ | 573 | 100 | 8 (1) | | | |
| 10 | O | 373 | 300 | 8 (2) | | | |
| 11 | Cl | 373 | −100 | 8 (1) | | | |

TABLE 10

| Node | | Coordinate | | Neighbor 1 | Neighbor 2 | Neighbor 3 | Neighbor 4 |
|---|---|---|---|---|---|---|---|
| No. | Kind | X | Y | Node (c) | Node (c) | Node (c) | Node (c) |
| 1 | C | 0 | 200 | 2 (1) | 6 (2) | 7 (1) | |
| 2 | C | 173 | 100 | 1 (1) | 3 (2) | 8 (1) | |
| 3 | C | 173 | −100 | 2 (2) | 4 (1) | | |
| 4 | C | 0 | −200 | 3 (1) | 5 (2) | 13 (1) | |
| 5 | C | −173 | −100 | 4 (2) | 6 (1) | | |
| 6 | C | −173 | 100 | 1 (2) | 5 (1) | | |
| 7 | CH₃ | 0 | 400 | 1 (1) | | | |
| 8 | C | 373 | 100 | 2 (1) | 9 (1) | 10 (2) | |

TABLE 10-continued

| Node | | Coordinate | | Neighbor 1 | Neighbor 2 | Neighbor 3 | Neighbor 4 |
|---|---|---|---|---|---|---|---|
| No. | Kind | X | Y | Node (c) | Node (c) | Node (c) | Node (c) |
| 9 | CH$_3$ | 573 | 100 | 8 (1) | | | |
| 10 | O | 373 | 300 | 8 (2) | | | |
| 13 | CH | 0 | −400 | 4 (1) | 14 (1) | 15 (1) | |
| 14 | CH$_3$ | −100 | −573 | 13 (1) | | | |
| 15 | CH$_3$ | 100 | −573 | 13 (1) | | | |
| 11 | Cl | 373 | −100 | | | | |
| 12 | H | 273 | 273 | | | | |

EXAMPLE 3

Beckmann rearrangement

The reaction is represented by the schematic equation.

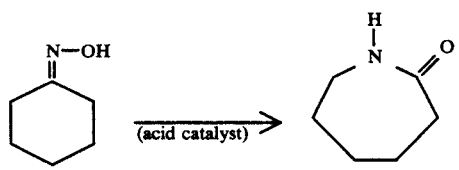  (Eq. 4)

An imaginary transition structure (ITS 4) for the Beckmann rearrangement and structural formulae of the starting stage and the product stage, which were obtained by subjecting ITS 4 to PS module and PP module, are represented as follows.

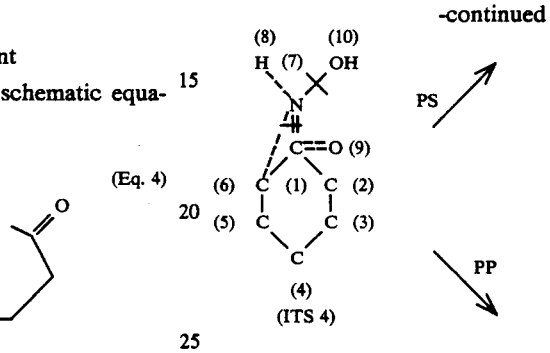

(ITS 4)

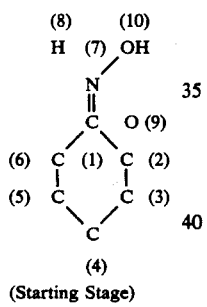

(Starting Stage)

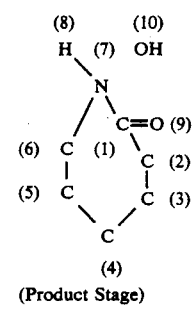

(Product Stage)

A connection table corresponding to ITS 4 was prepared. The connection table is set forth in Table 11, which includes information on the two-dimensional coordinate (xy-coordinate) of each node. Further, the connection table was subjected to PS module and PP module to obtain connection tables for the starting stage and the product stage. The results are respectively set forth in Tables 12 and 13.

TABLE 11

| Node | | Coordinate | | Neighbor 1 | Neighbor 2 | Neighbor 3 | Neighbor 4 |
|---|---|---|---|---|---|---|---|
| No. | Kind | X | Y | Node (a, b) | Node (a, b) | Node (a, b) | Node (a, b) |
| 1 | C | 0 | 200 | 2 (1 + 0) | 6 (1 − 1) | 7 (2 − 1) | 9 (0 + 2) |
| 2 | C | 173 | 100 | 1 (1 + 0) | 3 (1 + 0) | | |
| 3 | C | 173 | −100 | 2 (1 + 0) | 4 (1 + 0) | | |
| 4 | C | 0 | −200 | 3 (1 + 0) | 5 (1 + 0) | | |
| 5 | C | −173 | −100 | 4 (1 + 0) | 6 (1 + 0) | | |
| 6 | C | −173 | 100 | 1 (1 − 1) | 5 (1 + 0) | 7 (0 + 1) | |
| 7 | N | 0 | 400 | 1 (2 − 1) | 6 (0 + 1) | 8 (0 + 1) | 10 (1 − 1) |
| 8 | H | −100 | 573 | 7 (0 + 1) | | | |
| 9 | O | 173 | 300 | 1 (0 + 2) | | | |
| 10 | OH | 100 | 573 | 7 (1 − 1) | | | |

TABLE 12

| Node | | Coordinate | | Neighbor 1 | Neighbor 2 | Neighbor 3 | Neighbor 4 |
|---|---|---|---|---|---|---|---|
| No. | Kind | X | Y | Node (a) | Node (a) | Node (a) | Node (a) |
| 1 | C | 0 | 200 | 2 (1) | 6 (1) | 7 (2) | |
| 2 | C | 173 | 100 | 1 (1) | 3 (1) | | |
| 3 | C | 173 | −100 | 2 (1) | 4 (1) | | |
| 4 | C | 0 | −200 | 3 (1) | 5 (1) | | |
| 5 | C | −173 | −100 | 4 (1) | 6 (1) | | |
| 6 | C | −173 | 100 | 1 (1) | 5 (1) | | |
| 7 | N | 0 | 400 | 1 (2) | 10 (1) | | |

TABLE 12-continued

| Node | | Coordinate | | Neighbor 1 | Neighbor 2 | Neighbor 3 | Neighbor 4 |
|---|---|---|---|---|---|---|---|
| No. | Kind | X | Y | Node (a) | Node (a) | Node (a) | Node (a) |
| 10 | OH | 100 | 573 | 7 (1) | | | |
| 8 | H | −100 | 573 | | | | |
| 9 | O | 173 | 300 | | | | |

TABLE 13

| Node | | Coordinate | | Neighbor 1 | Neighbor 2 | Neighbor 3 | Neighbor 4 |
|---|---|---|---|---|---|---|---|
| No. | Kind | X | Y | Node (c) | Node (c) | Node (c) | Node (c) |
| 1 | C | 0 | 200 | 2 (1) | 7 (1) | 9 (2) | |
| 2 | C | 173 | 100 | 1 (1) | 3 (1) | | |
| 3 | C | 173 | −100 | 2 (1) | 4 (1) | | |
| 4 | C | 0 | −200 | 3 (1) | 5 (1) | | |
| 5 | C | −173 | −100 | 4 (1) | 6 (1) | | |
| 6 | C | −173 | 100 | 5 (1) | 7 (1) | | |
| 7 | N | 0 | 400 | 1 (1) | 6 (1) | 8 (1) | |
| 8 | H | −100 | 573 | 7 (1) | | | |
| 9 | O | 173 | 300 | 1 (2) | | | |
| 10 | OH | 100 | 573 | | | | |

EXAMPLE 4

Methylation reaction of cycloheptanone

The reaction is represented by the schematic equation.

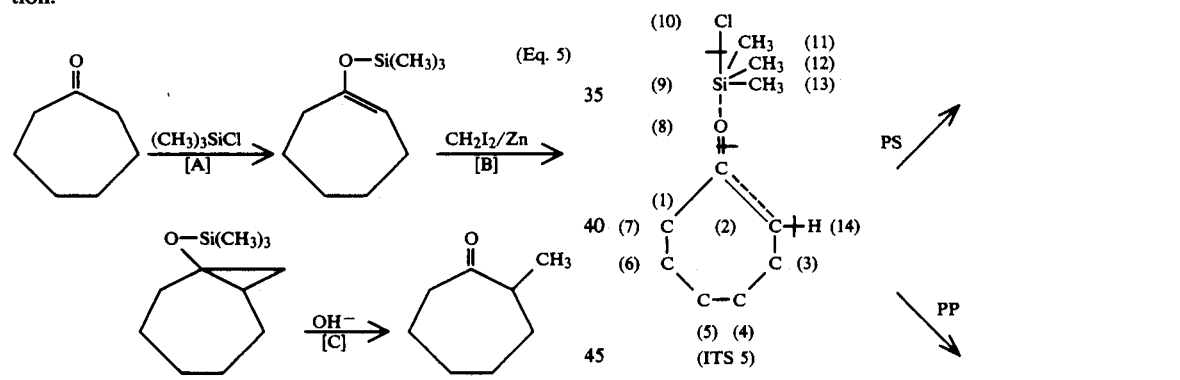

(Eq. 5)

(1) An imaginary transition structure (ITS 5) for the reaction at step [A] was prepared on the basis of both the structural formulae of the starting material and the product. Then, ITS 5 was subjected to PS module and PP module to obtain the structural formulae of the starting stage and the product stage. The results are shown as follows.

A connection table corresponding to ITS 5 was prepared. The connection table is set forth in Table 14, which includes information on the two-dimensional coordinate (xy-coordinate) of each node. Further, the connection table was subjected to PS module and PP module to obtain connection tables for the starting stage and the product stage. The results are respectively set forth in Tables 15 and 16.

TABLE 14

| Node | | Coordinate | | Neighbor 1 | Neighbor 2 | Neighbor 3 | Neighbor 4 | Neighbor 5 |
|---|---|---|---|---|---|---|---|---|
| No. | Kind | X | Y | Node (a,b) | Node (a,b) | Node (a,b) | Node (a,b) | Node (a,b) |
| 1 | C | 0 | 200 | 2 (1 + 1) | 7 (1 + 0) | 8 (2 − 1) | | |
| 2 | C | 173 | 100 | 1 (1 + 1) | 3 (1 + 0) | 14 (1 − 1) | | |
| 3 | C | 173 | −100 | 2 (1 + 0) | 4 (1 + 0) | | | |
| 4 | C | 100 | −286 | 3 (1 + 0) | 5 (1 + 0) | | | |
| 5 | C | −100 | −286 | 4 (1 + 0) | 6 (1 + 0) | | | |
| 6 | C | −173 | −100 | 5 (1 + 0) | 7 (1 + 0) | | | |
| 7 | C | −173 | 100 | 1 (1 + 0) | 6 (1 + 0) | | | |
| 8 | O | 0 | 400 | 1 (2 − 1) | 9 (0 + 1) | | | |
| 9 | Si | 0 | 600 | 8 (0 + 1) | 10 (1 − 1) | 11 (1 + 0) | 12 (1 + 0) | 13 (1 + 0) |
| 10 | Cl | 0 | 800 | 9 (1 − 1) | | | | |
| 11 | CH$_3$ | 100 | 773 | 9 (1 + 0) | | | | |
| 12 | CH$_3$ | 173 | 700 | 9 (1 + 0) | | | | |
| 13 | CH$_3$ | 200 | 600 | 9 (1 + 0) | | | | |
| 14 | H | 314 | −41 | 2 (1 − 1) | | | | |

TABLE 15

| Node | | Coordinate | | Neighbor 1 | Neighbor 2 | Neighbor 3 | Neighbor 4 |
|---|---|---|---|---|---|---|---|
| No. | Kind | X | Y | Node (a) | Node (a) | Node (a) | Node (a) |
| 1 | C | 0 | 200 | 2 (1) | 7 (1) | 8 (2) | |
| 2 | C | 173 | 100 | 1 (1) | 3 (1) | 14 (1) | |
| 3 | C | 173 | −100 | 2 (1) | 4 (1) | | |
| 4 | C | 100 | −286 | 3 (1) | 5 (1) | | |
| 5 | C | −100 | −286 | 4 (1) | 6 (1) | | |
| 6 | C | −173 | −100 | 5 (1) | 7 (1) | | |
| 7 | C | −173 | 100 | 1 (1) | 6 (1) | | |
| 8 | O | 0 | 400 | 1 (2) | | | |
| 14 | H | 314 | −41 | 2 (1) | | | |
| 9 | Si | 0 | 600 | 10 (1) | 11 (1) | 12 (1) | 13 (1) |
| 10 | Cl | 0 | 800 | 9 (1) | | | |
| 11 | CH$_3$ | 100 | 773 | 9 (1) | | | |
| 12 | CH$_3$ | 173 | 700 | 9 (1) | | | |
| 13 | CH$_3$ | 200 | 600 | 9 (1) | | | |

TABLE 16

| Node | | Coordinate | | Neighbor 1 | Neighbor 2 | Neighbor 3 | Neighbor 4 |
|---|---|---|---|---|---|---|---|
| No. | Kind | X | Y | Node (c) | Node (c) | Node (c) | Node (c) |
| 1 | C | 0 | 200 | 2 (2) | 7 (1) | 8 (1) | |
| 2 | C | 173 | 100 | 1 (2) | 3 (1) | | |
| 3 | C | 173 | −100 | 2 (1) | 4 (1) | | |
| 4 | C | 100 | −286 | 3 (1) | 5 (1) | | |
| 5 | C | −100 | −286 | 4 (1) | 6 (1) | | |
| 6 | C | −173 | −100 | 5 (1) | 7 (1) | | |
| 7 | C | −173 | 100 | 1 (1) | 6 (1) | | |
| 8 | O | 0 | 400 | 1 (1) | 9 (1) | | |
| 9 | Si | 0 | 600 | 8 (1) | 11 (1) | 12 (1) | 13 (1) |
| 11 | CH$_3$ | 100 | 773 | 9 (1) | | | |
| 12 | CH$_3$ | 173 | 700 | 9 (1) | | | |
| 13 | CH$_3$ | 200 | 600 | 9 (1) | | | |
| 10 | Cl | 0 | 800 | | | | |
| 14 | H | 314 | −41 | | | | |

(2) An imaginary transition structure (ITS 6) for the reaction at step [B] was prepared on the basis of both the structural formulae of the starting material and the product. Then, ITS 6 was subjected to PP module to obtain the structural formula of the product stage. The results are shown as follows.

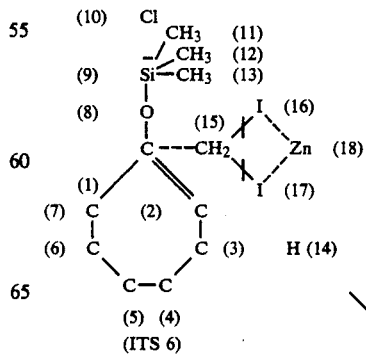

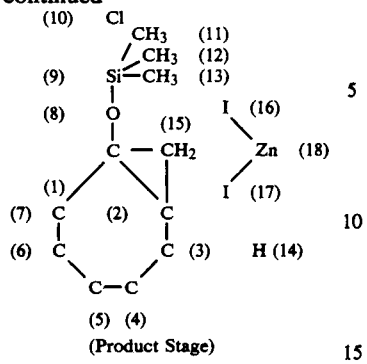

(Product Stage)

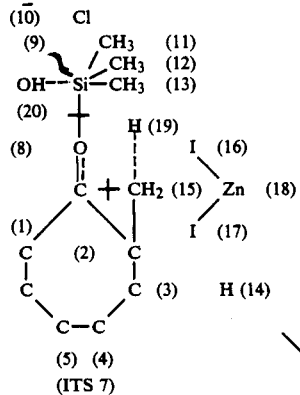

(ITS 7)

A connection table corresponding to ITS 6 was prepared. The connection table is set forth in Table 17, which includes information on the two-dimensional coordinate (xy-coordinate) of each node.

TABLE 17

| Node | | Coordinate | | Neighbor 1 | Neighbor 2 | Neighbor 3 | Neighbor 4 | Neighbor 5 |
|---|---|---|---|---|---|---|---|---|
| No. | Kind | X | Y | Node (a,b) | Node (a,b) | Node (a,b) | Node (a,b) | Node (a,b) |
| 1 | C | 0 | 200 | 2 (2 − 1) | 7 (1 + 0) | 8 (1 + 0) | 15 (0 + 1) | |
| 2 | C | 173 | 100 | 1 (2 − 1) | 3 (1 + 0) | 15 (0 + 1) | | |
| 3 | C | 173 | −100 | 2 (1 + 0) | 4 (1 + 0) | | | |
| 4 | C | 100 | −286 | 3 (1 + 0) | 5 (1 + 0) | | | |
| 5 | C | −100 | −286 | 4 (1 + 0) | 6 (1 + 0) | | | |
| 6 | C | −173 | −100 | 5 (1 + 0) | 7 (1 + 0) | | | |
| 7 | C | −173 | 100 | 1 (1 + 0) | 6 (1 + 0) | | | |
| 8 | O | 0 | 400 | 1 (1 + 0) | 9 (1 + 0) | | | |
| 9 | Si | 0 | 600 | 8 (1 + 0) | 11 (1 + 0) | 12 (1 + 0) | 13 (1 + 0) | |
| 10 | Cl | 0 | 800 | | | | | |
| 11 | $CH_3$ | 100 | 773 | 9 (1 + 0) | | | | |
| 12 | $CH_3$ | 173 | 700 | 9 (1 + 0) | | | | |
| 13 | $CH_3$ | 200 | 600 | 9 (1 + 0) | | | | |
| 14 | H | 314 | −41 | | | | | |
| 15 | $CH_2$ | 200 | 200 | 1 (0 + 1) | 2 (0 + 1) | 16 (1 − 1) | 17 (1 − 1) | |
| 16 | I | 373 | 300 | 15 (1 − 1) | 18 (0 + 1) | | | |
| 17 | I | 373 | 100 | 15 (1 − 1) | 18 (0 + 1) | | | |
| 18 | Zn | 546 | 200 | 16 (0 + 1) | 17 (0 + 1) | | | |

(3) An imaginary transition structure (ITS 7) for the reaction at step [C] was prepared on the basis of both the structural formulae of the starting material and the product. Then, ITS 7 was subjected to PP module to obtain the structural formula of the product stage. The results are shown as follows.

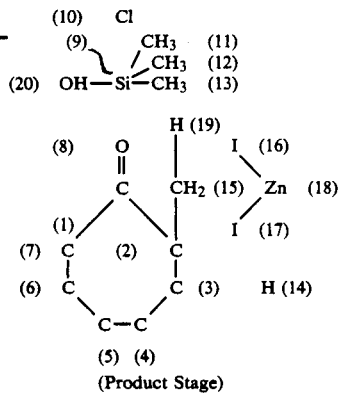

(Product Stage)

A connection table corresponding to ITS 7 was prepared. The connection table is set forth in Table 18, which includes information on the two-dimensional coordinate (xy-coordinate) of each node.

TABLE 18

| Node | | Coordinate | | Neighbor 1 | Neighbor 2 | Neighbor 3 | Neighbor 4 | Neighbor 5 |
|---|---|---|---|---|---|---|---|---|
| No. | Kind | X | Y | Node (a,b) | Node (a,b) | Node (a,b) | Node (a,b) | Node (a,b) |
| 1 | C | 0 | 200 | 2 (1 + 0) | 7 (1 + 0) | 8 (1 + 1) | 15 (1 − 1) | |
| 2 | C | 173 | 100 | 1 (1 + 0) | 3 (1 + 0) | 15 (1 + 0) | | |
| 3 | C | 173 | −100 | 2 (1 + 0) | 4 (1 + 0) | | | |
| 4 | C | 100 | −286 | 3 (1 + 0) | 5 (1 + 0) | | | |
| 5 | C | −100 | −286 | 4 (1 + 0) | 6 (1 + 0) | | | |
| 6 | C | −173 | −100 | 5 (1 + 0) | 7 (1 + 0) | | | |
| 7 | C | −173 | 100 | 1 (1 + 0) | 6 (1 + 0) | | | |
| 8 | O | 0 | 400 | 1 (1 + 0) | 9 (1 − 1) | | | |

TABLE 18-continued

| Node | | Coordinate | | Neighbor 1 | Neighbor 2 | Neighbor 3 | Neighbor 4 | Neighbor 5 |
|---|---|---|---|---|---|---|---|---|
| No. | Kind | X | Y | Node (a,b) | Node (a,b) | Node (a,b) | Node (a,b) | Node (a,b) |
| 9 | Si | 0 | 600 | 8 (1 − 1) | 11 (1 + 0) | 12 (1 + 0) | 13 (1 + 0) | 20 (0 + 1) |
| 10 | Cl | 0 | 800 | | | | | |
| 11 | $CH_3$ | 100 | 773 | 9 (1 + 0) | | | | |
| 12 | $CH_3$ | 173 | 700 | 9 (1 + 0) | | | | |
| 13 | $CH_3$ | 200 | 600 | 9 (1 + 0) | | | | |
| 14 | H | 314 | −41 | | | | | |
| 15 | $CH_2$ | 200 | 200 | 1 (1 − 1) | 2 (1 + 0) | 19 (0 + 1) | | |
| 16 | I | 373 | 300 | 18 (1 + 0) | | | | |
| 17 | I | 373 | 100 | 18 (1 + 0) | | | | |
| 18 | Zn | 546 | 200 | 16 (1 + 0) | 17 (1 + 0) | | | |
| 19 | H | 200 | 400 | 15 (0 + 1) | | | | |
| 20 | OH | −200 | 600 | 9 (0 + 1) | | | | |

(4) For the reaction at steps [A] and [B] represented by the schematic equation:

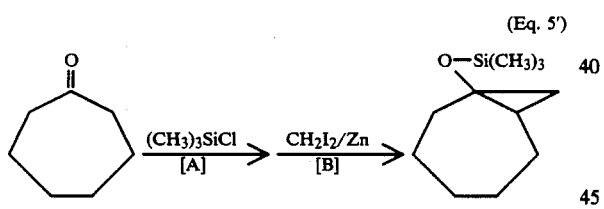
(Eq. 5')

an imaginary transition structure (ITS 8) was prepared on the basis of both the structural formulae of the starting material and the product. The result is shown as follows.

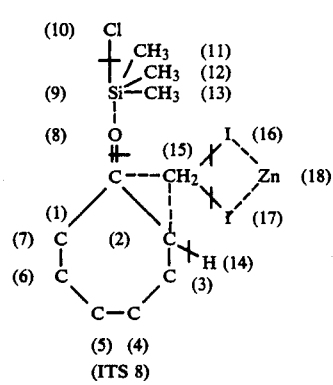

(ITS 8)

A connection table corresponding to ITS 8 was prepared. The connection table is set forth in Table 19, which includes information on the two-dimensional coordinate (xy-coordinate) of each node.

TABLE 19

| Node | | Coordinate | | Neighbor 1 | Neighbor 2 | Neighbor 3 | Neighbor 4 | Neighbor 5 |
|---|---|---|---|---|---|---|---|---|
| No. | Kind | X | Y | Node (a,b) | Node (a,b) | Node (a,b) | Node (a,b) | Node (a,b) |
| 1 | C | 0 | 200 | 2 (1 + 0) | 7 (1 + 0) | 8 (2 − 1) | 15 (0 + 1) | |
| 2 | C | 173 | 100 | 1 (1 + 0) | 3 (1 + 0) | 14 (1 − 1) | 15 (0 + 1) | |
| 3 | C | 173 | −100 | 2 (1 + 0) | 4 (1 + 0) | | | |
| 4 | C | 100 | −286 | 3 (1 + 0) | 5 (1 + 0) | | | |
| 5 | C | −100 | −286 | 4 (1 + 0) | 6 (1 + 0) | | | |
| 6 | C | −173 | −100 | 5 (1 + 0) | 7 (1 + 0) | | | |
| 7 | C | −173 | 100 | 1 (1 + 0) | 6 (1 + 0) | | | |
| 8 | O | 0 | 400 | 1 (2 − 1) | 9 (0 + 1) | | | |
| 9 | Si | 0 | 600 | 8 (0 + 1) | 10 (1 − 1) | 11 (1 + 0) | 12 (1 + 0) | 13 (1 + 0) |
| 10 | Cl | 0 | 800 | 9 (1 − 1) | | | | |
| 11 | $CH_3$ | 100 | 773 | 9 (1 + 0) | | | | |
| 12 | $CH_3$ | 173 | 700 | 9 (1 + 0) | | | | |
| 13 | $CH_3$ | 200 | 600 | 9 (1 + 0) | | | | |
| 14 | H | 314 | −41 | 2 (1 − 1) | | | | |
| 15 | $CH_2$ | 200 | 200 | 1 (0 + 1) | 2 (0 + 1) | 16 (1 − 1) | 17 (1 − 1) | |
| 16 | I | 373 | 300 | 15 (1 − 1) | 18 (0 + 1) | | | |
| 17 | I | 373 | 100 | 15 (1 − 1) | 18 (0 + 1) | | | |
| 18 | Zn | 546 | 200 | 16 (0 + 1) | 17 (0 + 1) | | | |

(5) For the reaction at steps [A], [B] and [C] represented by the schematic equation:

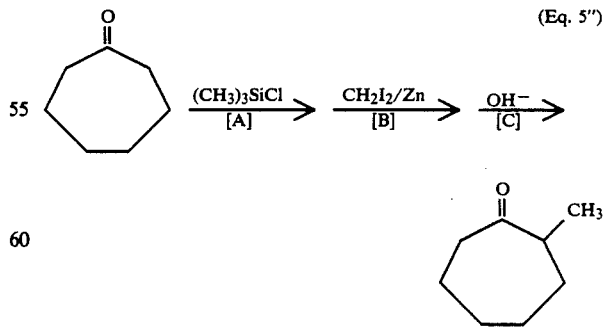
(Eq. 5")

an imaginary transition structure (ITS 9) was prepared on the basis of both the structural formulae of the starting material and the product. The result is shown as follows.

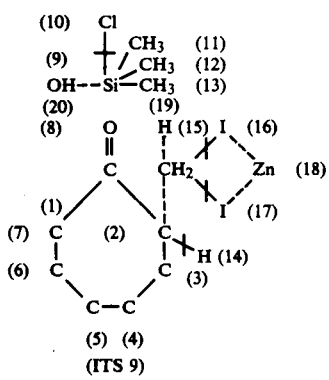

(ITS 9)

A connection table corresponding to ITS 9 was prepared. The connection table is set forth in Table 20, which includes information on the two-dimensional coordinate (xy-coordinate) of each node.

TABLE 20

| Node | | Coordinate | | Neighbor 1 | Neighbor 2 | Neighbor 3 | Neighbor 4 | Neighbor 5 |
|---|---|---|---|---|---|---|---|---|
| No. | Kind | X | Y | Node (a,b) | Node (a,b) | Node (a,b) | Node (a,b) | Node (a,b) |
| 1 | C | 0 | 200 | 2 (1 + 0) | 7 (1 + 0) | 8 (2 + 0) | | |
| 2 | C | 173 | 100 | 1 (1 + 0) | 3 (1 + 0) | 14 (1 − 1) | 15 (0 + 1) | |
| 3 | C | 173 | −100 | 2 (1 + 0) | 4 (1 + 0) | | | |
| 4 | C | 100 | −286 | 3 (1 + 0) | 5 (1 + 0) | | | |
| 5 | C | −100 | −286 | 4 (1 + 0) | 6 (1 + 0) | | | |
| 6 | C | −173 | −100 | 5 (1 + 0) | 7 (1 + 0) | | | |
| 7 | C | −173 | 100 | 1 (1 + 0) | 6 (1 + 0) | | | |
| 8 | O | 0 | 400 | 1 (2 + 0) | | | | |
| 9 | Si | 0 | 600 | 10 (1 − 1) | 11 (1 + 0) | 12 (1 + 0) | 13 (1 + 0) | 20 (0 + 1) |
| 10 | Cl | 0 | 800 | 9 (1 − 1) | | | | |
| 11 | CH$_3$ | 100 | 773 | 9 (1 + 0) | | | | |
| 12 | CH$_3$ | 173 | 700 | 9 (1 + 0) | | | | |
| 13 | CH$_3$ | 200 | 600 | 9 (1 + 0) | | | | |
| 14 | H | 314 | −41 | 2 (1 − 1) | | | | |
| 15 | CH$_2$ | 200 | 200 | 2 (0 + 1) | 16 (1 − 1) | 17 (1 − 1) | 19 (0 + 1) | |
| 16 | I | 373 | 300 | 15 (1 − 1) | 18 (0 + 1) | | | |
| 17 | I | 373 | 100 | 15 (1 − 1) | 18 (0 + 1) | | | |
| 18 | Zn | 546 | 200 | 16 (0 + 1) | 17 (0 + 1) | | | |
| 19 | H | 200 | 400 | 15 (0 + 1) | | | | |
| 20 | OH | −200 | 600 | 9 (0 + 1) | | | | |

I claim:

1. A method of storing information of an organic reaction in which a reaction of at least one starting material to give at least one reaction product is involved which comprises steps:

topologically superposing a chemical structural formula of the starting material or a combination of chemical structural formulae of the starting materials on a chemical structural formula of the reaction product or a combination of chemical structural formulae of the reaction products to give an imaginary transition structure;

classifying each bond linking two nodes of the imaginary transition structure into the following three groups: (1) bond linking two nodes appearing both in the formulae of the starting material and the reaction product, (2) bond linking two nodes appearing only in the formula of the starting material, and (3) bond linking two nodes appearing only in the formula of the reaction product;

denoting said bonds (1), (2) and (3) using a pair of integers (a, b), in which the integer a is bond multiplicity of the corresponding bond of the formula of the starting material and the integer b is difference in the bond multiplicity between the formula of the reaction product and the formula of the starting material;

representing nodes, neighboring nodes, and bonds linking a node and its neighboring node in the form of a connection table wherein said bonds are represented using the pair of integers (a, b), and storing the connection table in a recording material.

2. The method of claim 1, wherein the step of representing nodes, neighboring nodes and bonds includes a procedure of incorporating information on two-dimensional or three dimensional coordinate of each node in the connection table.

3. The method of claim 1, wherein the step of representing nodes, neighboring nodes and bonds includes a procedure of giving a title of the chemical reaction to the connection table.

4. The method of claim 1, wherein the step of storing the connection table further includes a procedure for storing a structural diagram of the chemical reaction which shows structural change of the starting material to the reaction product.

* * * * *